(12) United States Patent
Chan et al.

(10) Patent No.: US 7,843,562 B2
(45) Date of Patent: Nov. 30, 2010

(54) DETECTION OF BIOMOLECULES USING POROUS BIOSENSORS AND RAMAN SPECTROSCOPY

(75) Inventors: Selena Chan, Sunnyvale, CA (US); Tae-Woong Koo, Cupertino, CA (US)

(73) Assignee: Intel Corporation, Santa Clara, CA (US)

( * ) Notice: Subject to any disclaimer, the term of this patent is extended or adjusted under 35 U.S.C. 154(b) by 662 days.

(21) Appl. No.: 11/700,919

(22) Filed: Feb. 1, 2007

(65) Prior Publication Data

US 2008/0108131 A1 May 8, 2008

Related U.S. Application Data

(62) Division of application No. 10/748,390, filed on Dec. 29, 2003, now Pat. No. 7,271,896.

(51) Int. Cl.
*G01J 3/44* (2006.01)

(52) U.S. Cl. ............... 356/301; 356/454; 435/6; 435/283.1; 435/287.8; 435/288.7; 422/68.1; 422/82.05

(58) Field of Classification Search ............ None
See application file for complete search history.

(56) References Cited

U.S. PATENT DOCUMENTS

| | | | |
|---|---|---|---|
| 6,248,539 | B1 | 6/2001 | Ghadiri et al. |
| 6,514,767 | B1 | 2/2003 | Natan |
| 7,226,733 | B2 * | 6/2007 | Chan et al. ............ 435/6 |
| 2002/0093651 | A1 * | 7/2002 | Roe ..................... 356/301 |
| 2002/0192680 | A1 * | 12/2002 | Chan et al. ............ 435/6 |
| 2004/0150818 | A1 * | 8/2004 | Armstrong et al. ...... 356/301 |

FOREIGN PATENT DOCUMENTS

WO   03106943   12/2003

OTHER PUBLICATIONS

Chan et al., Nanoscale microcavities for biomedical sensor applications, 2000, Proc of SPIE, 3912, p. 23-34.*
Doering et al., "Spectroscopic Tags Using Dye-Embeded Nanoparticles and Surface-Enhanced Raman Scattering", Nat. Phys. Sci., 1973, vol. 241, pp. 22-24.

(Continued)

*Primary Examiner*—N. Yang
(74) *Attorney, Agent, or Firm*—Pillsbury Winthrop Shaw Pittman LLP (57) ABSTRACT

The invention provides methods used to analyze the contents of a biological sample, such as blood serum, with cascade Raman sensing. A fluorescence producing nanoporous biosensor having probes that bind specifically to known analytes is contacted with a biological sample and one or more bound complexes coupled to the porous semiconductor structure are formed. The bound complexes are contacted with a Raman-active probe that binds specifically to the bound complexes and the biosensor is illuminated to generate fluorescent emissions from the biosensor. These fluorescent emissions generate Raman signals from the bound complexes. The Raman signals produced by the bound complexes are detected and the Raman signal associated with a bound protein-containing analyte is indicative of the presence of the protein-containing compound in the sample. The invention methods are useful to provide a protein profile of a patient sample. The invention also provides detection systems useful to practice the invention methods.

16 Claims, 6 Drawing Sheets

OTHER PUBLICATIONS

Mulvaney et al., "Glass-coated, Analyte-Tagged Nanoparticles: A New Tagging System Based on Detection with Surface-Enhanced Raman Scattering", Langmuir, 2003, vol. 19, pp. 4784-4790.

Chan et al., "Porous Silicon Microcavities for Biosensing Applications", Phys. Stat. Sol., 2000, vol. 182, pp. 541-546.

Voldman et al., "Microfabrication in Biology and Medicine", Annu. Rev. Biomed. Engl., 1999, vol. 1, pp. 401-425.

Craighead, "Nanoelectromechanical Systems", Science, 2000, vol. 290, pp. 1532-1535.

* cited by examiner

RF1    ROX
       |
       GTAGACCTCGAATGCATGATC    FAM    (SEQ ID NO:1)
                           |

AT3    CATCTGGAGCTTACGTACTAG --NH2    (SEQ ID NO:2)
                         |
                         TAMRA

AT11   CATCTGGAGCTTACGTACTAG --NH2    (SEQ ID NO:3)
                  |
                  TAMRA

AT19   CATCTGGAGCTTACGTACTAG --NH2    (SEQ ID NO:4)
       |
       TAMRA

FIG. 5

FIG. 6

DETECTION OF BIOMOLECULES USING POROUS BIOSENSORS AND RAMAN SPECTROSCOPY

CROSS-REFERENCE TO RELATED APPLICATION

This application is a divisional of U.S. Ser. No. 10/748,390, filed on Dec. 29, 2003, the contents of which are incorporated herewith.

FIELD OF THE INVENTION

This invention relates generally to porous biosensors useful for identifying the presence of a biomolecule in a sample and, more particularly, this invention relates to the use of Raman spectroscopy and nanoporous semiconductor-based biosensors for determining the presence of biomolecules in a sample.

BACKGROUND OF THE INVENTION

Ever increasing attention is being paid to detection and analysis of low concentrations of analytes in various biologic and organic environments. Qualitative analysis of such analytes is generally limited to the higher concentration levels, whereas quantitative analysis usually requires labeling with a radioisotope or fluorescent reagent. Such procedures are generally time consuming and inconvenient.

Solid-state sensors and particularly biosensors have received considerable attention lately due to their increasing utility in chemical, biological, and pharmaceutical research as well as disease diagnostics. In general, biosensors consist of two components: a highly specific recognition element and a transducing structure that converts the molecular recognition event into a quantifiable signal. Biosensors have been developed to detect a variety of biomolecular complexes including oligonucleotide pairs, antibody-antigen, hormone-receptor, enzyme-substrate and lectin-glycoprotein interactions. Signal transductions are generally accomplished with electrochemical field-effect transistor, optical absorption, fluorescence or interferometric devices.

It is known that the intensity of the visible reflectivity changes of a porous silicon film can be utilized in a simple biological sensor, as disclosed in U.S. Pat. No. 6,248,539 to Ghadiri et al. As disclosed therein, the detection and measurement of wavelength shifts in the interference spectra of a porous semiconductor substrate, such as a silicon substrate, make possible detection, identification and quantification of small molecules. While such a biological sensor is certainly useful, detection of a reflectivity shift is complicated by the presence of a broad peak rather than one or more sharply defined luminescent peaks.

Various sensors that include a porous multilayer semiconductor structure having layers of alternating porosity have been developed. Upon binding of an analyte molecule, a detectable change occurs in a refractive index of the semiconductor structure to signal binding of the sensor to the analyte. The central layer of such a multilayered structure positioned between upper and lower layers (Bragg reflectors), forms a microcavity resonator. This microcavity resonator confines the luminescence generated in the central layer of the microcavity by the two layers that act as Bragg reflectors so that the photoluminescence spectrum is composed of multiple sharp and narrow peaks with Full-Width Half-Maximum, or FWHM, values of about 3 nm (Chan et al., Phys. Stat. Sol. A 182:541-546 (2000). Upon a refractive index change, the photoluminescent spikes shift, thereby generating a detectable differential signal. However, the binding event provides only approximate information regarding the nature of the molecule that binds.

Raman spectroscopy or surface plasmon resonance has also been used seeking to achieve the goal of sensitive and accurate detection or identification of individual molecules from biological samples. When light passes through a medium of interest, a certain amount of the light becomes diverted from its original direction in a phenomenon known as scattering. Some of the scattered light also differs in frequency from the original excitatory light, due to the absorption of light and excitation of electrons to a higher energy state, followed by light emission at a different wavelength. The difference of the energy of the absorbed light and the energy of the emitted light matches the vibrational energy of the medium. This phenomenon is known as Raman scattering, and the method to characterize and analyze the medium or molecule of interest with the Raman scattered light is called Raman spectroscopy. The wavelengths of the Raman emission spectrum are characteristic of the chemical composition and structure of the Raman scattering molecules in a sample, while the intensity of Raman scattered light is dependent on the concentration of molecules in the sample.

It has been observed that molecules near roughened silver surfaces show enhanced Raman scattering of as much as two orders of magnitude or more. This surface enhanced Raman scattering (SERS) effect is related to the phenomenon of plasmon resonance, wherein metal nanoparticles or metal coatings exhibit a pronounced optical resonance in response to incident electromagnetic radiation, due to the collective coupling of conduction electrons in the metal. In essence, nanoparticles of gold, silver, copper and certain other metals can function to enhance the localized effects of electromagnetic radiation. Molecules located in the vicinity of such particles exhibit a much greater sensitivity for Raman spectroscopic analysis. SERS is the technique to utilize this surface enhanced Raman scattering effect to characterize and analyze biological molecules of interest.

Sodium chloride and lithium chloride have been identified as chemicals that enhance the SERS signal when applied to a metal nanoparticle or metal coated surface before or after the molecule of interest has been introduced. However, the technique of using these chemical enhancers has not proved sensitive enough to reliably detect low concentrations of analyte molecules, such as single nucleotides or proteins. Only one type of nucleotide, deoxyadenosine monophosphate, and only one type of protein, hemoglobin, have been detected at single molecule level. As a result SERS has not been viewed as suitable for analyzing the protein content of a complex biological sample, such as blood plasma.

Thus a need exists in the art for a method of biomolecule detection that provides information regarding the characteristics of the bound molecule and for reliably detecting and/or identifying individual molecules using a Raman spectroscopic analytical technique. In addition, there is also a need in the art for quick and simple means of qualitatively and quantitatively detecting biomolecules at low concentration levels.

BRIEF DESCRIPTION OF THE DRAWINGS

FIGS. 2A-D is a schematic representation of partial nanoporous silicon layers with primary antibody immobilized thereon. FIG. 2A again shows antigen bound to immobilized primary antibody immobilized in the nanoporous cavity.

FIGS. 3A-D provide a schematic flow chart showing exposure of the sensor of FIG. 2 to a Raman-active secondary antibody. FIG. 3C illustrates deposit of a thin silver layer on the top layer of the nanoporous cavity. The strong florescence emission generated by the nanoporous cavity in the sensor excites the Raman-active secondary antibody to generate a SERS signal as shown graphically in FIG. 3D a SERS signal.

DETAILED DESCRIPTION OF THE INVENTION

One aspect of the present invention relates to methods of using a biological sensor that includes a porous semiconductor structure and one or more first probes coupled to the porous semiconductor structure to bind specifically to desired analytes in a complex biological sample. When a second Raman-active probe construct is bound to complexes containing the first probes, the presence of the associated specific analyte in the sample is identified. The invention methods are particularly of use to obtain a protein profile of a patient sample.

In one embodiment, the invention provides methods for analyzing the contents of a biological sample by contacting a biological sample under suitable binding conditions with a nanoporous biosensor having a porous semiconductor structure with a central layer interposed between upper and lower layers, each of the upper and lower layers including up to 40 strata of alternating porosity; and one or more first probes coupled to the porous semiconductor structure, the one or more first probes binding specifically to an analyte in the sample to form one or more bound complexes. The bound complexes are contacted with a Raman-active probe under conditions suitable to promote specific binding thereof to the bound complexes and the biosensor is illuminated so as to cause fluorescent emissions from the biosensor, these emissions exciting Raman signals from the bound complexes. Raman signals produced by the bound complexes are detected and the Raman spectrum associated with a bound analyte indicates presence of the analyte in the sample.

Figure 1A:
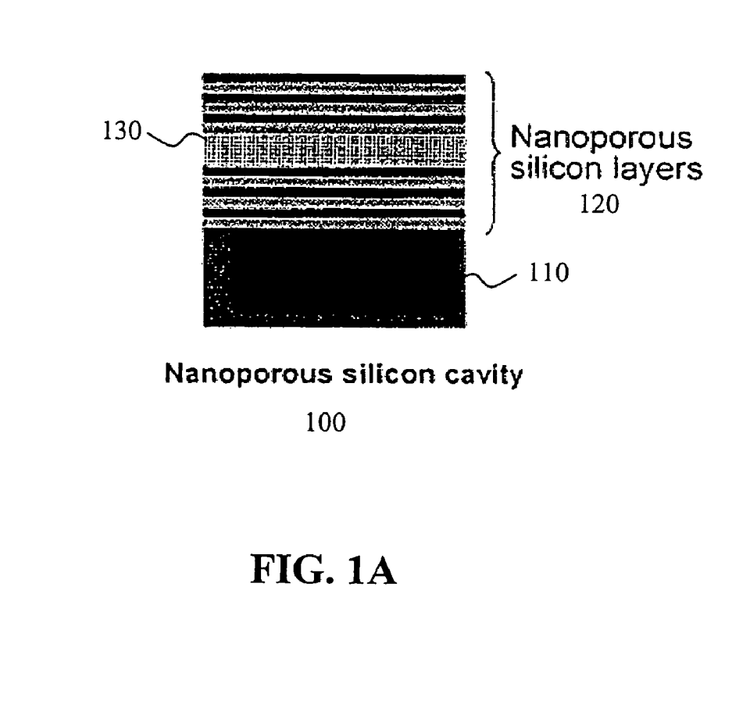
FIG. 1A is a schematic flow chart showing a nanoporous silicon cavity with multiple strata of alternating porosity situated on either side of a central layer.
Figure 1B:
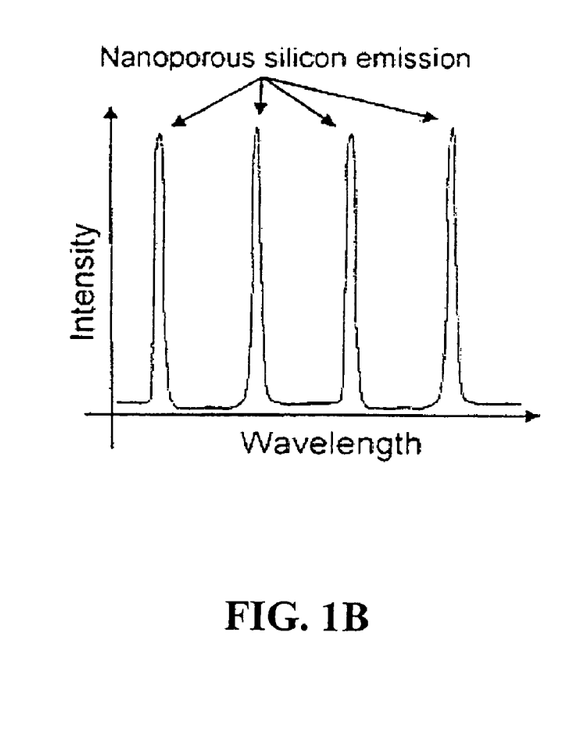
FIG. 1B is a graph illustrating fluorescence emissions from the nanoporous silicon cavity of FIG. 1A.
Figure 2A:
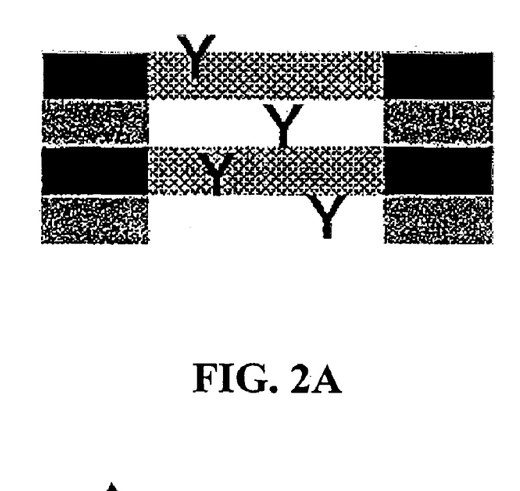
Figure 2B:
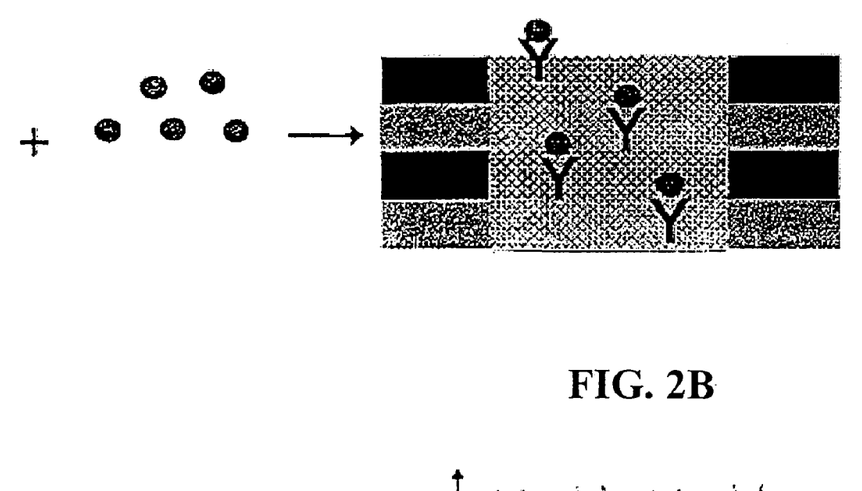
Figure 2C:
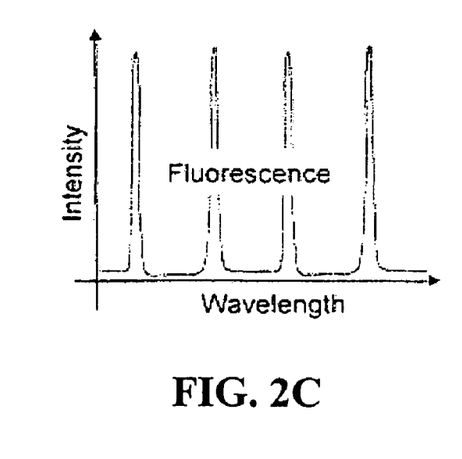
Figure 2D:
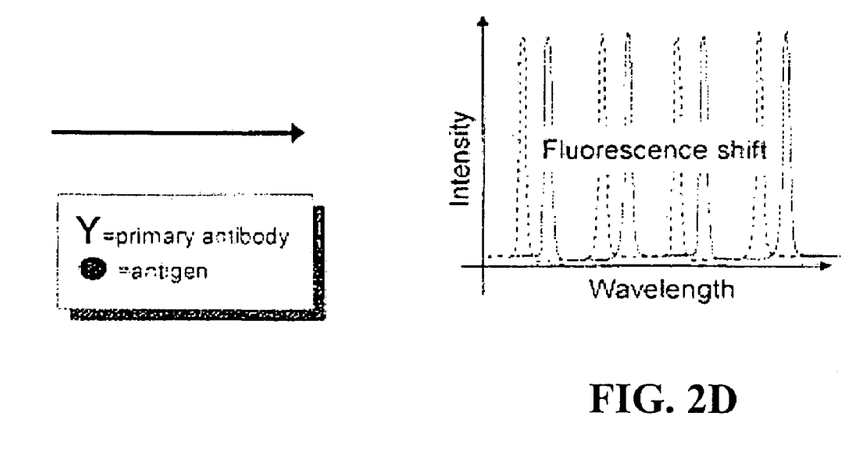

With reference to FIG. 1, nanoporous silicon cavity 100 comprises a silicon substrate 110 with multiple strata of alternating porosity 120 situated on either side of a central layer 130. The fluorescence emission produced upon irradiation of the nanoporous silicon cavity 100 is shown graphically in FIG. 1B.

In yet another embodiment, the invention provides methods for detecting the presence of a protein-containing analyte in a biological sample by contacting the sample under conditions effective to allow specific binding of a protein-containing analyte therein to at least one first probe coupled to a nanoporous biological sensor made of a nanoporous silicon structure having a central layer interposed between upper and lower layers, each of the upper and lower layers including up to 40 strata of alternating porosity, for example, 4 to 40 strata with about 8 to about 30 strata being presently considered most suitable to provide fewer, narrower peaks in the Raman signals than when fewer or more strata are employed. The number of strata in each of the upper and lower layers is selected within these ranges to produce reflective layers of desired reflectivity.

The binding of the first probes (e.g., primary antibodies) to analytes in the sample forms one or more bound complexes. The bound complexes are contacted with a Raman-active probe, such as a Raman-tagged secondary antibody as described herein, under conditions suitable to promote specific binding thereof to the bound complexes. The biosensor is illuminated so as to cause fluorescent emissions from the biosensor, and the emissions from the biosensor excite Raman signals from the bound complexes (FIGS. 3A-D). The Raman signals produced by the bound complexes are detected and the Raman signal associated with a bound protein-containing analyte is indicative of the presence and type of the protein-containing compound in the sample.

In yet another embodiment, the invention provides methods for analyzing the content of a biological sample by contacting a biological sample under suitable binding conditions with a nanoporous semiconductor sensor as described herein having one or more first probes attached that binding specifically to at least one analyte in the sample to form one or more bound complexes. The one or more bound complexes are contacted with a fluorescence-active probe under conditions suitable to promote specific binding thereof, the sensor is illuminated so as to cause fluorescent emissions from the sensor, the emissions generating secondary fluorescent emissions from the bound complexes; and the secondary fluorescent emissions produced by the bound complexes are detected. A secondary fluorescent emission associated with a bound analyte is indicative of presence and type of the analyte in the sample.

In another embodiment, the invention provides a detection system that includes a nanoporous biological sensor having a porous semiconductor structure comprising a central layer interposed between upper and lower layers that each include up to 40 strata of alternating porosity. The invention system further includes a source of illumination positioned to illuminate the biological sensor; and a detector positioned to capture Raman signals or fluorescence from complexes bound to the sensor. In one aspect, the source of illumination is a mercury or tungsten lamp.

A target molecule can also be detected directly without the need for a Raman-active or fluorescence-active second probe. Unique Raman and fluorescence signals have been observed emitting from DNA molecules of different sequence. It is also known that proteins generate different signals based upon their composition and conformation. Therein, in still another embodiment, the invention provides methods for analyzing the content of a biological sample by contacting a biological sample under suitable binding conditions with a nanoporous semiconductor sensor as described herein having one or more first probes coupled to the porous semiconductor structure, the one or more first probes binding specifically to at least one analyte in the sample to form one or more bound complexes; illuminating the sensor so as to cause optical emissions from the analytes in the bound complexes; and detecting the optical emissions produced by the analytes in the bound complexes; wherein the analytes are proteins or DNA and Raman or fluorescence signals emitted from the analytes provide information concerning the presence and type of analyte in a bound complex.

Suitable Raman-active tags that can be attached by known methods to probes, such as antibodies and receptors, to prepare the Raman-active probes used in the invention methods include those in Table I below.

TABLE 1

| Organic Compound | Abbreviation |
| --- | --- |
| 2-Aminopurine | AP |
| 2-Fluoroadenine | FA |
| 4-Amino-pyrazolo[3,4-d]pyrimidine | APP |
| 4-Pyridinecarboxaldoxime | PCA |
| 8-Azaadenine | AA |
| Adenine | A |
| 4-Amino-3,5-di-2-pyridyl-4H-1,2,4-triazole | AMPT |
| 6-(g,g-Dimethylallylamino)purine | DAAP |
| Kinetin | KN |
| N6-Benzoyladenine | BA |
| Zeatin | ZT |
| 4-Amino-2,1,3-benzothiadiazole | ABT |
| Acriflavine | AF |
| Basic blue 3 | BB |
| Methylene Blue | MB |
| 2-Mercapto-benzimidazole | MBI |
| 4-amino-6-mercaptopyrazolo[3,4-d]pyrimidine | AMPP |
| 6-Mercaptopurine | MP |
| 8-Mercaptoadenine (adenine thiol) | AT |
| 9-Aminoacridine | AN |
| Cyanine dyes | Cy3 |
| Ethidium bromide | Ebr |
| Fluorescein | FAM |
| Rhodamine Green | R110 |
| Rhodamine-6G | R6G |

In certain embodiments, the apparatus can comprise a micro-electromechanical system (MEMS). MEMS are integrated systems including mechanical elements, sensors, actuators, and electronics. All of those components can be manufactured by microfabrication techniques on a common chip, of a silicon-based or equivalent semiconductor substrate (e.g., Voldman et al., *Ann. Rev. Biomed. Eng.* 1:401-425, 1999). The sensor components of MEMS can be used to measure biological, chemical, optical and/or magnetic phenomena to detect Raman signals or fluorescence. The electronics can process the information from the sensors and control actuator components, such as pumps, valves, heaters, etc. thereby controlling the function of the MEMS.

The electronic components of MEMS can be fabricated using integrated circuit (IC) processes (e.g., CMOS or Bipolar processes). They can be patterned using photolithographic and etching methods for computer chip manufacture. The micromechanical components can be fabricated using compatible "micromachining" processes that selectively etch away parts of the silicon wafer or add new structural layers to form the mechanical and/or electromechanical components.

Basic techniques in MEMS manufacture include depositing thin films of material on a substrate, applying a patterned mask on top of the films by some lithographic methods, and selectively etching the films. A thin film can be in the range of a few nanometers to 100 micrometers. Deposition techniques of use can include chemical procedures such as chemical vapor deposition (CVD), electrodeposition, epitaxy and thermal oxidation and physical procedures like physical vapor deposition (PVD) and casting. Methods for manufacture of nanoelectromechanical systems can also be used (See, e.g., Craighead, *Science* 290:1532-36, 2000.)

In some embodiments, apparatus and/or detectors can be connected to various fluid filled compartments, for example microfluidic channels or nanochannels. These and other components of the apparatus can be formed as a single unit, for example in the form of a chip (e.g. semiconductor chips) and/or microcapillary or microfluidic chips. Alternatively, individual components can be separately fabricated and attached together. Any materials known for use in such chips can be used in the disclosed apparatus, for example silicon, silicon dioxide, polydimethyl siloxane (PDMS), polymethylmethacrylate (PMMA), plastic, glass, quartz, etc.

In one embodiment, individual miniaturized biosensors ranging in size from about one micrometer to about 15 nanometers in cross-sectional diameter can be arrayed together (e.g. on a common base) and detected by scanning across the biosensors. In such case, the biosensor may conveniently have a single type of probe for immobilizing a single known analyte (although multiple first probes can also be used).

Techniques for batch fabrication of chips are well known in computer chip manufacture and/or microcapillary chip manufacture. Such chips can be manufactured by any method known in the art, such as by photolithography and etching, laser ablation, injection molding, casting, molecular beam epitaxy, dip-pen nanolithography, chemical vapor deposition (CVD) fabrication, electron beam or focused ion beam technology or imprinting techniques. Non-limiting examples include conventional molding, dry etching of silicon dioxide; and electron beam lithography. Methods for manufacture of nanoelectromechanical systems can be used for certain embodiments. (See, e.g., Craighead, *Science* 290:1532-36, 2000.) Various forms of microfabricated chips are commercially available from, e.g., Caliper Technologies Inc. (Mountain View, Calif.) and ACLARA BioSciences Inc. (Mountain View, Calif.).

In certain embodiments, part or all of the apparatus can be selected to be transparent to electromagnetic radiation at the excitation and emission frequencies used for detection by, for example, Raman spectroscopy. Suitable components can be fabricated from materials such as glass, silicon, quartz or any other optically clear material. Surface modification of common chip materials such as glass, silicon, quartz and/or PDMS is known (e.g., U.S. Pat. No. 6,263,286). Such modifications can include, for example, coating with commercially available silanes with various functional moieties (e.g. polyethyleneoxide or acrylamide, etc).

In some embodiments, the first probe is a polynucleotide. The term "polynucleotide" is used broadly herein to mean a sequence of deoxyribonucleotides or ribonucleotides that are linked together by a phosphodiester bond. For convenience, the term "oligonucleotide" is used herein to refer to a polynucleotide that is used as a primer or a probe. Generally, an oligonucleotide useful as a probe or primer that selectively hybridizes to a selected nucleotide sequence is at least about 10 nucleotides in length, usually at least about 15 nucleotides in length, for example between about 15 and about 50 nucleotides in length.

A polynucleotide can be RNA or can be DNA, which can be a gene or a portion thereof, a cDNA, a synthetic polydeoxyribonucleic acid sequence, or the like, and can be single stranded or double stranded, as well as a DNA/RNA hybrid. In various embodiments, a polynucleotide, including an oligonucleotide (e.g., a probe or a primer) can contain nucleoside or nucleotide analogs, or a backbone bond other than a phosphodiester bond. In general, the nucleotides comprising a polynucleotide are naturally occurring deoxyribonucleotides, such as adenine, cytosine, guanine or thymine linked to 2'-deoxyribose, or ribonucleotides such as adenine, cytosine, guanine or uracil linked to ribose. However, a polynucleotide or oligonucleotide also can contain nucleotide analogs, including non-naturally occurring synthetic nucleotides or modified naturally occurring nucleotides. Such nucleotide analogs are well known in the art and commercially available, as are polynucleotides containing such nucleotide analogs (Lin et al., *Nucl. Acids Res.* 22:5220-5234 (1994); Jellinek et al., *Biochemistry* 34:11363-11372 (1995); Pagratis et al., *Nature Biotechnol.* 15:68-73 (1997)).

The covalent bond linking the nucleotides of a polynucleotide generally is a phosphodiester bond. However, the covalent bond also can be any of numerous other bonds, including a thiodiester bond, a phosphorothioate bond, a peptide-like bond or any other bond known to those in the art as useful for linking nucleotides to produce synthetic polynucleotides (see, for example, Tam et al., *Nucl. Acids Res.* 22:977-986 (1994); Ecker and Crooke, *BioTechnology* 13:351360 (1995)). The incorporation of non-naturally occurring nucleotide analogs or bonds linking the nucleotides or analogs can be particularly useful where the polynucleotide is to be exposed to an environment that can contain a nucleolytic activity, including, for example, a tissue culture medium or upon administration to a living subject, since the modified polynucleotides can be less susceptible to degradation.

As used herein, the term "selective hybridization" or "selectively hybridize," refers to hybridization under moderately stringent or highly stringent conditions such that a nucleotide sequence preferentially associates with a selected nucleotide sequence over unrelated nucleotide sequences to a large enough extent to be useful in identifying the selected nucleotide sequence. It will be recognized that some amount of non-specific hybridization is unavoidable, but is acceptable provided that hybridization to an analyte nucleotide sequence is sufficiently selective such that it can be distinguished over the non-specific cross-hybridization, for example, at least about 2-fold more selective, generally at least about 3-fold more selective, usually at least about 5-fold more selective, and particularly at least about 10-fold more selective, as determined, for example, by an amount of labeled oligonucleotide that binds to analyte nucleic acid molecule as compared to a nucleic acid molecule other than the analyte molecule, particularly a substantially similar (e.g., homologous) nucleic acid molecule other than the analyte nucleic acid molecule. Conditions that allow for selective hybridization can be determined empirically, or can be estimated based, for example, on the relative GC:AT content of the hybridizing oligonucleotide and the sequence to which it is to hybridize, the length of the hybridizing oligonucleotide, and the number, if any, of mismatches between the oligonucleotide and sequence to which it is to hybridize (see, for example, Sambrook et al., "Molecular Cloning: A laboratory manual (Cold Spring Harbor Laboratory Press 1989), incorporated in its entirety by reference).

An example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 68° C. (high stringency conditions). Washing can be carried out using only one of these conditions, e.g., high stringency conditions, or each of the conditions can be used, e.g., for 10-15 minutes each, in the order listed above, repeating any or all of the steps listed. However, as mentioned above, optimal conditions will vary, depending on the particular hybridization reaction involved, and can be determined empirically.

In some embodiments, the first probe and/or the second probe can include an antibody probe. As used herein, the term "antibody" is used in its broadest sense to include polyclonal and monoclonal antibodies, as well as antigen binding fragments of such antibodies. An antibody useful in a method of the invention, or an antigen binding fragment thereof, is characterized, for example, by having specific binding activity for an epitope of an analyte.

An antibody is utilized in the first probe attached to the biosensor in certain aspects of the invention and a secondary antibody (e.g., one that is a specific binding partner for a region of the antibody probe can be tagged with a Raman-active tag, as described herein, for use as the Raman-active in the invention methods. The term "antibody" as used herein refers to naturally occurring antibodies, including monoclonal antibodies, as well as non-naturally occurring antibodies. Non-limiting examples of non-naturally-occurring antibodies, include, for example, single chain antibodies, chimeric, bifunctional and humanized antibodies, as well as antigen-binding fragments thereof. Such non-naturally occurring antibodies can be constructed using solid phase peptide synthesis, can be produced recombinantly or can be obtained, for example, by screening combinatorial libraries consisting of variable heavy chains and variable light chains (see Huse et al., *Science* 246:1275-1281 (1989),). These and other methods of making, for example, chimeric, humanized, CDR-grafted, single chain, and bifunctional antibodies are well known to those skilled in the art (Winter and Harris, *Immunol. Today* 14:243-246, 1993; Ward et al., *Nature* 341: 544-546, 1989; Harlow and Lane, *Antibodies: A laboratory manual* (Cold Spring Harbor laboratory Press, 1988); Hilyard et al., *Protein Engineering: A practical approach* (IRL Press 1992); Borrabeck, *Antibody Engineering,* 2d ed. (Oxford University Press 1995)).

The term "binds specifically" or "specific binding activity," when used in reference to an antibody means that an interaction of the antibody and a particular epitope has a dissociation constant of at least about $1\times10^{-6}$, generally at least about $1\times10^{-7}$, usually at least about $1\times10^{-8}$, and particularly at least about $1\times10^{-9}$ or $1\times10^{-10}$ or less. As such, Fab, F(ab')$_2$, Fd and Fv fragments of an antibody that retain specific binding activity for an epitope of an antigen, are included within the definition of an antibody.

In the context of the invention, the term "ligand" denotes a naturally occurring specific binding partner of a receptor, a synthetic specific-binding partner of a receptor, or an appropriate derivative of the natural or synthetic ligands. The determination and isolation of ligands is well known in the art (Lerner, *Trends Neurosci.* 17:142-146, 1994)). As one of skill in the art will recognize, a molecule (or macromolecular complex) can be both a receptor and a ligand. In general, the binding partner having a smaller molecular weight is referred to as the ligand and the binding partner having a greater molecular weight is referred to as a receptor.

By "analyte" is meant any molecule or compound present in a biological sample. An analyte can be in the solid, liquid, gaseous or vapor phase. By "gaseous or vapor phase analyte" is meant a molecule or compound that is present, for example, as a contaminant in a biological sample. It will be recognized that the physical state of the gas or vapor phase can be changed by pressure, temperature as well as by affecting surface tension of a liquid by the presence of or addition of salts etc.

As indicated above, methods of the present invention, in certain aspects, detect binding of an analyte in a biological sample to a first probe attached to a semiconductor biosensor, as described herein. The analyte can be comprised of a member of a specific binding pair (sbp) and may be a ligand, which is monovalent (monoepitopic) or polyvalent (polyepitopic), usually antigenic or haptenic, and is a single compound or plurality of compounds which share at least one common epitopic or determinant site. The analyte can be a part of a cell such as a bacteria or a cell bearing a blood group antigen such as A, B, D, etc., or an HLA antigen or a microorganism, e.g., bacterium, fungus, protozoan, or virus. In certain aspects of the invention, the analyte is charged.

A member of a specific binding pair ("sbp member") is one of two different molecules, having an area on the surface or in a cavity which specifically binds to and is thereby defined as complementary with a particular spatial and polar organization of the other molecule. The members of the specific binding pair are referred to as ligand and receptor (antiligand) or analyte and probe. Therefore, a probe is a molecule that specifically binds an analyte. These will usually be members of an immunological pair such as antigen-antibody, although other specific binding pairs such as biotin-avidin, hormones-hormone receptors, nucleic acid duplexes, IgG-protein A, polynucleotide pairs such as DNA-DNA, DNA-RNA, and the like, are not immunological pairs but are included in the invention and the definition of sbp member.

Specific binding is the specific recognition of one of two different molecules for the other compared to substantially less recognition of other molecules. Generally, the molecules have areas on their surfaces or in cavities giving rise to specific recognition between the two molecules. Exemplary of specific binding are antibody-antigen interactions, enzyme-substrate interactions, polynucleotide interactions, and so forth.

Non-specific binding is non-covalent binding between molecules that is relatively independent of specific surface structures. Non-specific binding may result from several factors including hydrophobic interactions between molecules.

The invention methods may be used to detect the presence of a particular analyte, for example, a nucleic acid, oligonucleotide, protein, enzyme, antibody or antigen. The invention methods may also be used to screen bioactive agents, e.g. drug candidates, for binding to a particular analyte in a biological sample or to detect the presence of agents, such as pollutants, in a biological sample. As discussed above, any analyte for which a probe moiety, such as a peptide, protein, oligonucleotide or aptamer, may be designed can be detected using the invention methods.

The polyvalent ligand analytes will normally be poly(amino acids), e.g., polypeptides and proteins, polysaccharides, nucleic acids, and combinations thereof. Such combinations include components of bacteria, viruses, chromosomes, genes, mitochondria, nuclei, cell membranes and the like.

For the most part, the polyepitopic ligand analytes to which the subject invention can be applied will have a molecular weight of at least about 5,000, more usually at least about 10,000. In the poly(amino acid) category, the poly(amino acids) of interest will generally be from about 5,000 to 5,000,000 molecular weight, more usually from about 20,000 to 1,000,000 molecular weight; among the hormones of interest, the molecular weights will usually range from about 5,000 to 60,000 molecular weight.

The monoepitopic ligand analytes will generally be from about 100 to 2,000 molecular weight, more usually from 125 to 1,000 molecular weight. The analytes include drugs, metabolites, pesticides, pollutants, and the like. Included among drugs of interest are the alkaloids. Among the alkaloids are morphine alkaloids, which includes morphine, codeine, heroin, dextromethorphan, their derivatives and metabolites; cocaine alkaloids, which include cocaine and benzyl ecgonine, their derivatives and metabolites; ergot alkaloids, which include the diethylamide of lysergic acid; steroid alkaloids; iminazoyl alkaloids; quinazoline alkaloids; isoquinoline alkaloids; quinoline alkaloids, which include quinine and quinidine; diterpene alkaloids, their derivatives and metabolites.

The term analyte further includes polynucleotide analytes such as those polynucleotides defined below. These include m-RNA, r-RNA, t-RNA, DNA, DNA-RNA duplexes, etc. The term analyte also includes receptors that are polynucleotide binding agents, such as, for example, restriction enzymes, activators, repressors, nucleases, polymerases, histones, repair enzymes, chemotherapeutic agents, and the like, that can be detected using the invention methods.

The analyte may be a molecule found directly in a sample, such as a bodily fluid from a host. The sample can be examined directly or may be pretreated to render the analyte more readily detectible. Furthermore, the analyte of interest may be determined by detecting an agent probative of the analyte of interest such as a specific binding pair member complementary to the analyte of interest, whose presence will be detected only when the analyte of interest is present in a sample. Thus, the agent probative of the analyte becomes the analyte that is detected in an assay. The bodily fluid can be, for example, urine, blood, plasma, serum, saliva, semen, stool, sputum, cerebral spinal fluid, tears, mucus, and the like.

It is well known that Raman spectroscopy can monitor the conformational changes or secondary structures of proteins (Sane, S. et al., "structure perturbations on chromatographic surfaces", *Journal of Chromatography* A 849(1999) 149-159; and D. Ben-Amotz, et al., "New Dimensions in Proteomic Sensing", *Federation of Analytical Chemistry and Spectroscopic Societies Meeting*, Oct. 19-23, 2003, Fort Lauderdale, Fla.). Reference herein to detecting the "type of protein" using Raman signals refers to such conformational changes and/or secondary structure of protein-containing analytes.

A "protein-containing analyte" as the term is used herein encompasses such entities as antigens, peptides, polypeptides, proteins, gluco-proteins, lipid proteins, and the like.

The following paragraphs include further details regarding exemplary applications of the invention methods. It will be understood that numerous additional specific examples of applications that utilize the invention methods can be identified using the teachings of the present specification. One of skill in the art will recognize that many interactions between polypeptide first probes and their analyte molecules can be detected using the invention methods. In another example, an enzyme first probe can be used to detect interaction of the enzyme with a substrate analyte in the sample.

Another group of exemplary methods uses the invention methods to detect one or more analyte nucleic acid in a sample. Such a method is useful, for example, for detection of infectious agents within a clinical sample, detection of an amplification product derived from genomic DNA or RNA or message RNA, or detection of a gene (cDNA) insert within a clone. For certain methods aimed at detection of an analyte polynucleotide, an oligonucleotide probe is synthesized using methods known in the art. The oligonucleotide probe is then used as a first probe to be attached to the biosensor. The oligonucleotide first probe is used in a hybridization reaction to allow specific binding of the oligonucleotide probe to an analyte polynucleotide in the sample. The complex formed by binding of the oligonucleotide probe can then be detected using fluorescence emission, Raman spectroscopy or SERS as described herein. Detection of the specific binding of the known oligonucleotide probe to an analyte oligonucleotide in the sample provides information regarding the nucleotide sequence of the analyte polynucleotide.

The porous semiconductor structure used in the invention methods can be formed onto any suitable substrate (e.g., on a chip, wafer, etc.). The porous semiconductor structure includes a central layer (a microcavity) interposed between upper and lower layers, each of the upper and lower layers including strata of alternating porosity. The upper and lower layers form Bragg reflectors.

Semiconductors that can be used to form the porous semiconductor structure can be a single semiconductor material, a combination of semiconductor materials that are unmixed, or a mixture of semiconductor materials. The semiconductor can be one that is photoluminescent in its porous state. By virtue of the thickness of the active layer confined by the Bragg reflectors (e.g., the upper and lower layers), the emitted photoluminescence spectrum is composed of multiple sharp and narrow peaks. The light can be in the visible portion of the electromagnetic spectrum (e.g., 350-800 nm), the infrared region (e.g., 800-3000 nm), and the ultraviolet region (e.g., 50-350 nm). These wavelengths are only exemplary and can vary according to the type of semiconductor material(s) used to form the porous semiconductor structure, the thickness thereof, as well as the porosity thereof (including pore size). For the invention methods, light in the visible portion of the electromagnetic spectrum is usually preferred.

Preferred semiconductors which can be used to form the porous semiconductor structure include, without limitation, silicon and silicon alloys. The semiconductor is amenable to galvanic etching processes which can be used to form the porous structure. These semiconductor materials can include p-doped silicon (e.g., $(CH_3)_2Zn$, $(C_2H_5)_2Zn$, $(C_2H_5)_2Be$, $(CH_3)_2Cd$, $(C_2H_5)_2Mg$, B, Al, Ga, In), n-doped (e.g., $H_2Se$, $H_2S$, $CH_3Sn$, $(C_2H_5)_3S$, $SiH_4$, $Si_2H_6$, P, As, Sb) silicon, intrinsic or undoped silicon, polysilicon, alloys of these materials with, for example, germanium in amounts of up to about 10% by weight, mixtures of these materials, and semiconductor materials based on Group III element nitrides.

Two primary advantages make porous silicon (or nanoscale silicon) an attractive material for biosensing applications. First, its enormous surface area ranges from about 90 $m^2/cm^3$ to about 783 $m^2/cm^3$, which provides numerous sites for many potential species to attach. Second, its eye-detectable, room temperature luminescence spans the visible spectrum, which makes it an effective transducer.

The porous semiconductor structure can range in thickness from about 1 to about 30 microns. Typically, the thickness will vary inversely according to the desired porosity (e.g., higher porosity structures will be thicker than lower porosity structures at constant etching time) as well as according to the wavelength of light to be detected (e.g., structures which are used with shorter wavelength light can be thinner than structures which are used with longer wavelength light, assuming constant index of refraction of the porous semiconductor material over the spectral range).

The pores (or cavities) in the porous semiconductor structure are typically sized in terms of their nominal "diameter" notwithstanding the fact that they are somewhat irregular in shape and vary in diameter from one strata to another. These diameters range from about 2 nm to about 2000 nm, with diameters of about 10 to about 100 nm being preferred for visible light, about 2 to about 50 nm diameters being preferred for ultraviolet light, and 100 to 2000 nm being preferred for infrared light. The nominal pore diameter should also be selected based upon the size of the analyte molecule to be detected.

As noted above, the porosity of the structure, including its central layer, will vary inversely according to its thickness at constant etching time. Typically, the porosity of the central layer is about 50 to about 90 percent, although slightly lower or higher porosity may be attained for specific applications. For most applications, the porosity is preferably about 65 to about 85 percent for structural stability.

The upper and lower layers individually contain strata of alternating porosity, e.g., higher and lower porosity strata, relative to the adjacent strata. The upper layer and lower layer can be symmetrical (e.g., having the same configuration, including the number of strata) or they can be different (e.g., having different strata configurations in number and/or porosity). Typically, the total number of strata is six or more (e.g., three or more high porosity strata and three or more low porosity strata in an alternating configuration).

The lower porosity strata have a porosity that is less than the porosity of their adjacent higher porosity strata. For example, the lower porosity strata can have a porosity of about 35 to about 70 percent, or about 40 to about 60 percent while the higher porosity strata can have a porosity of about 55 to about 80 percent, or between about 60 to about 80 percent.

Within each of the upper and lower layers on opposite sides of the central layer, the low porosity and high porosity strata need not be the same throughout. Thus, different low porosity strata and different high porosity strata can be present within a single upper or lower layer. Alternatively, the low porosity strata and the high porosity strata can be substantially consistent within the upper and lower layers.

Reflection of light at the top and bottom of the porous semiconductor structure used in the invention methods results in an interference pattern that is related to the effective optical thickness of the structure. Binding of an analyte molecule to its corresponding probe, immobilized on the surfaces of the porous semiconductor structure, results in a change in refractive index of the structure and is detected as a corresponding shift in the interference pattern. The refractive index for the porous semiconductor structure in use is related to the index of the porous semiconductor structure and the index of the materials present (contents) in the pores. The index of refraction of the contents of the pores changes when the concentration of analyte species in the pores changes. For example, if the analyte molecule is an organic molecule that has a refractive index larger than that of the semiconductor structure, binding of the analyte molecule replaces a species of lower index of refraction (air or other vapor medium) and would be expected to lead to an increase in the overall value for index of refraction. An increase in index should result in a shift in the interference pattern wavelengths to longer values; e.g., a bathochromic or "red" shift.

Methods for making such a porous semiconductor structure are well known in the art. See, for example Published U.S. Patent Application 20020192680. A roughened metal surface can be produced using one of several methods.

To form a biological sensor from the porous semiconductor structure, one or more probes that bind to an analyte molecule are coupled to the porous semiconductor structure. The one or more probes each include (i) one or more semiconductor-binding groups which enable them to be coupled to the semiconductor structure (either directly or via a coupling agent) and (ii) one or more analyte-binding groups that bind to an analyte molecule. Although not limited to such, the one or more semiconductor-binding groups are typically hydroxyl groups. The one or more analyte-binding groups can include, without limitation, an amino group, a thiol, a hydroxyl, an alkyl chain, an ester, a carboxylic acid, an aromatic, a heterocycle, or a combination thereof.

Suitable first probes generally include, without limitation, non-polymeric small molecules, antibodies, antigens, polynucleotides, oligonucleotides, receptors, ligands, and the like.

Exemplary non-polymeric small molecules suitable for use as a first probe include, without limitation: avidin, peptidomimetic compounds, and vancomycin. One class of peptidomimetic compounds is disclosed in U.S. patent application Ser. No. 09/568,403 to Miller et al., filed May 10, 2000. A peptido-mimetic compound that binds to lipopolysaccharide is a tetratryptophan ter-cyclopentane. Other peptidomimetic compounds can also be employed.

Exemplary polypeptides suitable for use as a first probe include, without limitation, a receptor for a cell surface molecule or fragment thereof; a lipid A receptor; an antibody or fragment thereof; peptide monobodies of the type disclosed in U.S. patent application Ser. No. 09/096,749 to Koide, filed Jun. 12, 1998, and U.S. patent application Ser. No. 10/006,760 to Koide, filed Nov. 19, 2001; a lipopolysacchardide-binding polypeptide; a peptidoglycan-binding polypeptide; a carbohydrate-binding polypeptide; a phosphate-binding polypeptide; a nucleic acid-binding polypeptide; and polypeptides that specifically bind to a protein-containing analyte. In one embodiment, the first probes are antibodies specific for a particular protein-containing analyte or a particular class or family of protein-containing analytes.

Exemplary oligonucleotide first probes can be DNA, RNA, or modified (e.g., propynylated) oligonucleotides of the type disclosed in Barnes et al., J. Am. Chem. Soc. 123:4107-4118 (2001), and Barnes et al., J. Am. Chem. Soc. 123:9186-9187 (2001). The oligonucleotide probes can be any length that is suitable to provide specificity for the intended analyte. Typically, oligonucleotide probes that do not contain modified nucleotides will be at least about 12 to about 100 nucleotides in length. For oligonucleotides that contain modified bases, a length of at least 7 nucleotides, up to about 100 nucleotides is suitable.

Analyte molecules that can be bound by the one or more first probes include, without limitation: proteins (including without limitation enzymes, antibodies or fragments thereof), glycoproteins, peptidoglycans, carbohydrates, lipoproteins, a lipoteichoic acid, lipid A, phosphates, nucleic acids that are expressed by certain pathogens (e.g., bacteria, viruses, multicellular fungi, yeasts, protozoans, multicellular parasites, etc.), or organic compounds such as naturally occurring toxins or organic warfare agents, etc. These analyte molecules can be detected from any source, including bodily fluids, food samples, water samples, homogenized tissue from organisms, etc.

A number of strategies are available for attaching the one or more first probes to the surface of the porous semiconductor structure, depending upon the type of probe that is ultimately to be attached thereto. Because of the porosity of the semiconductor structure, the probes can be bound to the exposed surfaces of the semiconductor structure throughout its central layer and its upper and lower layers.

The available strategies for attaching the one or more first probes include, without limitation, covalently bonding a probe to the surface of the semiconductor structure, ionically associating the probe with the surface of the semiconductor structure, adsorbing the probe onto the surface of the semiconductor structure, or the like. Such association can also include covalently or noncovalently attaching the probe to another moiety (of a coupling agent), which in turn is covalently or non-covalently attached to the surface of the semiconductor structure.

Basically, the oxidized and hydrolyzed surface of the semiconductor structure is first functionalized (e.g., primed) with a coupling agent which is attached to the surface thereof. This is achieved by providing a coupling agent precursor and then covalently or non-covalently binding the coupling agent precursor to the surface of the semiconductor structure. Once the semiconductor surface has been functionalized, the probe is exposed to the functional group attached to the semiconductor surface under conditions effective to (i) covalently or non-covalently bind to the coupling agent or (ii) displace the coupling agent such that the first probe covalently or non-covalently binds directly to the semiconductor surface. The binding of the first probe to the semiconductor structure is carried out under conditions that are effective to allow the one or more analyte-binding groups thereon to remain available for binding to the analyte molecule.

Suitable coupling agent precursors include, without limitation, silanes functionalized with an epoxide group, a thiol, or an alkenyl; and halide containing compounds.

Silanes include a first moiety which binds to the surface of the semiconductor structure and a second moiety which binds to the probe. Preferred silanes include, without limitation, 3-glycidoxypropyltrialkoxy-silanes with C1-6 alkoxy groups, trialkoxy(oxiranylalkyl)silanes with C2-12 alkyl groups and C1-6 alkoxy groups, 2-(1,2-epoxycyclohexyl)ethyltr-ialkoxysilane with C1-6 alkoxy groups, 3-butenyl trialkoxysilanes with C1-6 alkoxy groups, alkenyltrialkoxysilanes with C2-12 alkenyl groups and C1-6 alkoxy groups, tris[(1-methylethenyl)oxy]3-oxiranylalkyl silanes with C2-12 alkyl groups, [5-(3,3-dimethyloxiranyl)-3-methyl-2-pentenyl]trialkoxysilane with C1-6 alkoxy groups, (2,3-oxiranediyidi-2,1-ethanediyl)b-is-triethoxysilane, trialkoxy[2-(3-methyloxiranyl)alkyl]silane with C1-6 alkoxy groups and C2-12 alkyl groups, trimethoxy[2-[3-(17,17,17-trifluoroheptadecyl)oxiranyl]ethyl]silane, tributoxy[3-[3-(chloromethyl)oxiranyl]-2-methylpropyl]silane, and combinations thereof. Silanes can be coupled to the semiconductor structure according to a silanization reaction scheme for which the conditions are well known to those of skill in the art.

Halides can also be coupled to the semiconductor structure under conditions well known to those of skill in the art.

Thereafter, the one or more first probes are bound to the semiconductor structure according to the type of functionality provided by the coupling agent. Typically, first probes are attached to the coupling agent or displace the coupling agent for attachment to the semicoductor structure in aqueous conditions or aqueous/alcohol conditions. For example, epoxide functional groups can be opened to allow binding of amino groups, thiols or alcohols; and alkenyl functional groups can be reacted to allow binding of alkenyl groups. Where a halide coupling agent is employed, the halide coupling agent is typically displaced upon exposing the functionalized semiconductor structure to one or more probes that contain alcohol groups as the semiconductor-binding groups.

Where the one or more first probes contain two or more analyte-binding groups, it is possible that the analyte-binding groups may also interact and bind to the functionalized surface of the semiconductor structure. To preclude this from occurring, the functionalized porous semiconductor structure can also be exposed to a blocking agent to minimize the number of sites where the one or more probes can attach to the surface of the semiconductor structure. Exposure to the blocking agent can be carried out prior to exposing the functionalized surface of the semiconductor structure to the probes or simultaneous therewith, although simultaneous exposure is generally preferred. The blocking agents can be structurally similar to the first probes except that they lack an analyte-binding group or the blocking agents can be simple end-capping agents. By way of example, an amino acid alkyl ester (e.g., glycine methyl ester, glycine ethyl ester, 3-alanine methyl ester, etc.) blocking agent can be introduced to an epoxide-functionalized semiconductor structure with the amino group of glycine opening the epoxide ring and covalently binding to the coupling agent.

Detectable changes in the refractive index of the biological sensor occur upon binding of the one or more first probes to the analyte molecule, depending on the sensitivity of the type of detector employed. Many widely available detectors afford the detection of photoluminescent peak emission shifts of about 2 nm or greater.

When quantitative detection is desired, the size of the photoluminescent peak emission shift correlates with the amount of bound analyte that appears in the pores following exposure thereof to a sample containing the analyte. Knowing the maximal amount of analyte that can bind to a biological, e.g., the number of available analyte-binding groups on the surface-bound first probes and the maximal shift that can be achieved under those conditions, it is possible to predict a quantitative concentration of the analyte in a sample based on the detected shift that occurs.

For use as a microarray detector suitable for use in detecting analytes contained in a biological sample, such as blood urine, blood, plasma, serum, saliva, semen, stool, sputum, cerebral spinal fluid, tears, or mucus a number of locations or zones on the biosensor are functionalized to include first probes that are specific for desired analytes. For example, antibodies selected to bind to a specific molecule or specific type of molecule containing an epitope can be located in a discrete zone of the biosensor. The one or more first probes at each of these locations can be the same (binding to the same analyte) or different (being selected to bind to different analytes).

The invention methods use the above properties of the semiconductor biosensor to detect multiple layers of biomolecular interactions, termed "cascade sensing" or "cascade binding." In cascade binding, an analyte, once bound in a complex with the first probe, becomes a binding analyte for a Raman-active or fluorescence active probe that binds to either molecule in the bound complex. As those of skill in the art will appreciate, sensing based on cascade binding reduces the percentage of false positives produced by non-specific binding of the probe as compared with methods that base results upon binding of a single probe.

A Raman-active probe is any probe that includes a Raman-active tag and is suitable to bind to a desired bound complex or first probe. For example, in one embodiment, the first probe is a primary antibody selected for its specific binding to a known protein-containing analyte in the sample, and the Raman-active probe can be a secondary antibody that binds to the primary antibody and bears a Raman-active tag. In embodiments wherein the first probes attached to the sensor are a plurality of antibodies specific for a variety of known protein-containing analytes, the Raman-active probes can be secondary antibodies bearing a Raman-active tag that binds to the primary antibodies, as is known in the art. In this embodiment, the Raman-active probe can be a secondary antibody specific for a particular type of antibody, for example IgG or IgA, and the Raman-active probes used can all be the same. Alternatively, different Raman-active antibodies can also be used as the Raman-active probes.

Raman-active tags suitable for inclusion in the Raman-active probes, e.g., by binding to a secondary antibody, include Raman-active fluorophores and organic molecules. Organic molecules suitable for use as the Raman-active tag in the invention methods include adenine or an analog thereof, such as 4-amino-pyrazolo(3,4-d)pyrimidine, 2-fluoroadenine, N6-benzolyadenine, kinetin, dimethyl-allyl-aminoadenine, zeatin, bromo-adenine, 8-aza-adenine, 8-azaguanine, 6-mercaptopurine, 4-amino-6-mercaptopyrazolo(3,4-d)pyrimidine, 8-mercaptoadenine, or 9-amino-acridine. A Raman-active organic compound will commonly have a molecular weight less than about 300 Daltons. The Raman-active tag can also be or contain a fluorescent label.

Figure 3A:
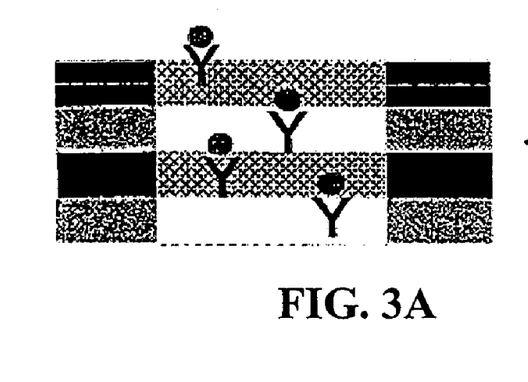
FIG. 3A again shows antigen bound to primary antibody immobilized in the nanoporous cavity.
Figure 3B:
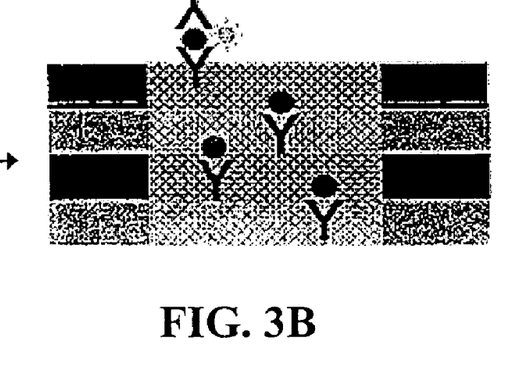
FIG. 3B illustrates Raman active secondary antibody bound to the antigen.
Figure 3C:
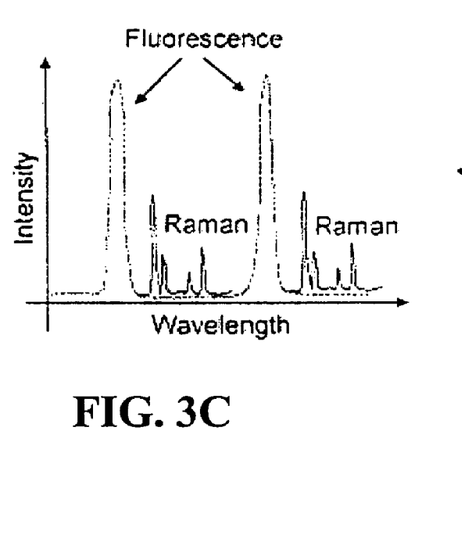
FIG. 3C illustrates deposit of a thin silver layer on the top layer of the nanoporous cavity. The emission due to increase in the effective optical thickness of the layers in the sensor produced upon antigen binding to the immobilized primary antibody is shown graphically in FIG. 2D.
Figure 3D:
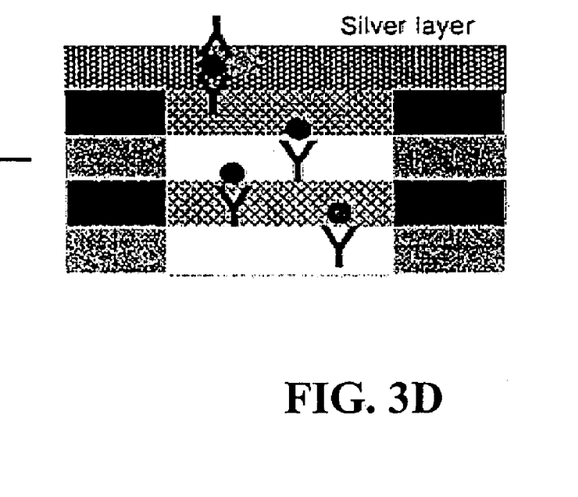

To enhance the Raman spectra produced by Raman-active probes, in one embodiment of the invention methods, it is contemplated to transform the Raman-active probes to SERS-active probes in situ after binding of the Raman-active probes to the complex of the first probes and analytes. To this purpose, a layer of a transparent metal, such as gold or silver, is deposited over the roughened surface of the upper layer of the sensor and/or the bound complexes thereon to provide a metal layer with a roughened surface (FIG. 3C). For example, the metal layer can be formed by contacting the surface to be covered with a colloidal solution of metal cations in the presence of a reducing agent to cause formation of a layer of nanoparticles of the metal. The metal layer should have a thickness of about one-half the wavelength of the illuminating light source, for example from about 15 nm to about 500 nm, such as about 100 nm to about 200 nm.

A roughened metal surface can be produced using one of several methods. The roughness features are on the order of tens of nanometers; small, compared to the wavelength of the incident excitation radiation. The small size of the particles allows the excitation of the metal particle's surface plasmon to be localized on the particle. Metal roughness features at the metal surface can be developed in a number of ways; for example; vapor deposition of metal particles or application of metal colloids onto the upper layer of the biosensor. Since the surface electrons of the metal are confined to the particle, whose size is small, the plasmon excitation is also confined to the roughness feature. The resulting electromagnetic field of the plasmon is very intense, greatly enhancing the SERS signal as compared to a Raman signal. It has been estimated that less than 1% of photons are inelastically Raman scattered. However, in embodiments of the invention methods wherein the intensity of Raman signal from a scattering molecule is greatly enhanced under SERS conditions, low concentrations of a Raman-active analyte can be detected at concentrations as low as pico- and femto-molar. In some circumstances, the invention methods can be used to detect the presence of a single analyte molecule in a complex biological sample, such as blood serum by contacting the upper surface of the biosensor with metal cations under conditions suitable to reduce the metal cations. A thin layer of metal nanoparticles such as silver or gold can be deposited.

For example, metal specimen can be sputtered or evaporated for direct deposition on the biosensor. Alternatively, an aqueous solution is prepared containing suitable metal cations and a reducing agent and subjected to conditions that reduce the metallic cations in situ to form neutral, colloidal metal nanoparticles in a thin layer over the surface of the biosensor and the molecules attached thereon.

Raman-active organic tags will be adsorbed onto the metal during colloid formation. Due to close proximity of the Raman-active tags to the metal layer, surface enhanced Raman scattering (SERS) will be produced by the tags upon irradiation.

The invention methods differ from other types of Raman spectroscopy or SERS techniques in which Raman-active molecules are directly irradiated by a suitable light source and the Raman or SERS spectra detected. In the invention methods, the Raman active molecules are indirectly irradiated by fluorescence produced by the biosensor itself upon irradiation of the biosensor. The Raman or SERS signal is generated from the Raman-active probe (e.g., antibody) by excitation of the Raman-active tag therein with fluorescence emitted from the biosensor.

Due to the repeated fluorescence emissions from the irradiated biosensor, the Raman signal is generated over the spectral range.

In one embodiment of the invention methods, a Fabry-Perot interferometer can be used to transmit only certain lines of the SERS or Raman signal, and the transmitted signal can be collected using a single channel detector. For example, a range of spectrum can be collected by tuning the transmission line of the interferometer. Raman signals generated under different excitation wavelengths yield different spectral information regarding the bound biomolecule of interest.

Figure 4:
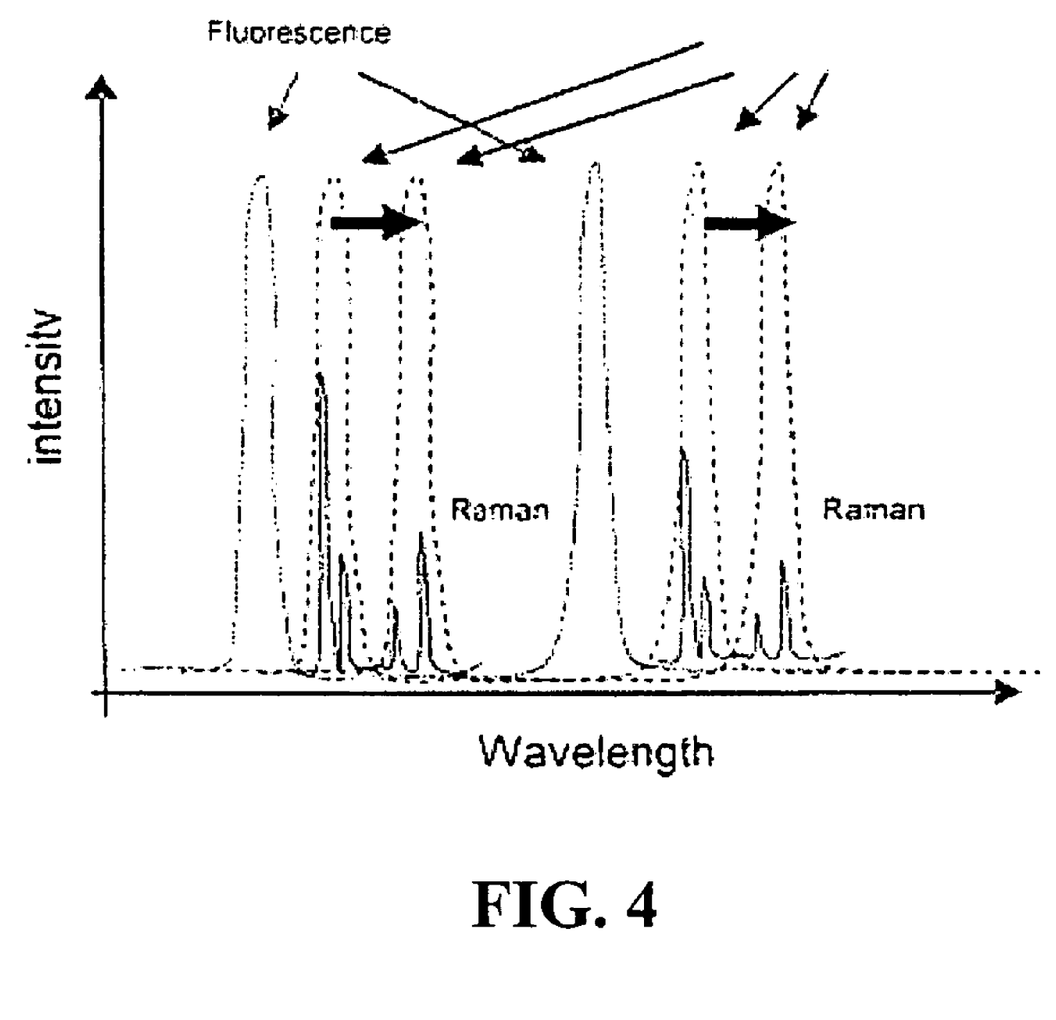
FIG. 4 is a graphical representation of the SERS signal generated from the secondary antibody bound to the sensor as shown in FIG. 3. Due to repeated fluorescence emissions from the sensor, the Raman signal is generated over the spectral range. By collecting light transmitted through a Fabry-Perot interferometer, the transmission line can be shifted for scanning as shown.

The Fabry-Perot interferometer, high resolution, high throughput optical spectrometer works on the principle of constructive interference. Given a monochromatic point source, imaged through a conjugate lens pair (with the interferometer in between), the rays either constructively or destructively interfere in the interferometer. Thus a bright or dark spot is seen at the image plane. With a distributed monochromatic source, different rays travel different path lengths inside the cavity, and the Fabry-Perot interferometer becomes an angle filter, resulting in the characteristic circular "Airy" fringe pattern. Change the plate spacing slightly, or tune the source, and the "phase" of the Airy pattern changes. Used in scan mode, the Fabry-Perot inferometer can be used to image photons from a single probe volume onto a detector. The mirrors are then scanned via piezoelectric actuators. This technique effectively moves the constructive-interference passband of the interferometer, allowing scanning across a spectral feature of the photons scattered from the luminescent flow under study (FIG. 4).

In another embodiment, the invention provides a system comprising the biosensor, a source of illumination (e.g., argon, cadmium, helium, or nitrogen laser and accompanying optics) positioned to illuminate the biological sensor, and a detector (e.g., collecting lenses, monochrometer, and detector) positioned to capture photoluminescent emissions from the biological sensor and to detect changes in photoluminescent emissions from the biological sensor. The source of illumination and the detector can both be present in a Raman spectrometer. A computer with an appropriate microprocessor can be coupled to the detector to receive data from the spectrometer and analyze the data to compare the photoluminescence before and after exposure of the biological sensor to an analyte.

In yet another embodiment, the present invention relates to methods of detecting an analyte in a sample by exposing the biological sensor to a sample under conditions effective to allow binding of an analyte in the sample to the one or more probes of the biological sensor. After such exposure, it is determined whether the biological sensor emits a photoluminescent emission pattern that has been altered, indicating the presence of the analyte in the sample. Two types of alteration can be observed. The porous silicon films display Fabry-Perot fringes in their white-light reflection spectrum (See "Luminescent Color Image Generation on Porous Si" Doan, V. V.; Sailor, M. J. Science 1992, 256, 1791-1792). Upon exposure to the appropriate complementary binding pair, binding occurs and is observed as a shift in wavelength of the Fabry-Perot fringes. In addition there is a shift in the resonance features of the microcavities.

To determine whether a shift has occurred, a first (baseline) photoluminescent emission pattern is measured prior to exposure to a sample, and after exposure to the sample, a second photoluminescent emission pattern is measured and the first and second emission patterns are compared. A shift as little as about 2 nm can indicate the presence of the analyte in the sample. Typically, the size of the shift will depend on the size of the analyte to be recognized and its concentration within the sample. This determination can be performed using the detection device as described above.

Samples that can be examined using the invention methods include blood, water, a suspension of solids (e.g., food particles, soil particles, etc.) in an aqueous solution, or a cell suspension from a clinical isolate (such as a tissue homogenate from a mammalian patient). If the sample includes cells, it can be desirable but not essential to treat the sample prior to its exposure to the biological sensor in a manner effective to disrupt the cellular membrane. This can be achieved by chemical means that do not modify the structure of the analyte sought to be detected, by mechanical means (French press), by sonication, or by freezing (and thawing).

From all of the above, it should be appreciated that the invention methods for screening biological samples can be used with appropriate probes for purposes of defining protein-protein interactions for proteomics, defining molecular interaction partners involved in the regulation of gene transcription events, for genomic analysis, for metabonomic analysis, and in general for screening drugs to determine their interactions with particular proteins or nucleic acids, as well as for screening combinatorial libraries to determine species that bind to a particular probe (which itself can be a biochemical analyte for therapeutic or preventative treatments).

In addition the invention methods can be used to create a protein profile of a bodily sample from a particular individual or to create a library of such protein profiles for the purpose of determining differences in the protein profiles of a particular type of bodily fluid obtained from a patient having a known disease and a comparable sample obtained from a healthy individual. Ultimately, such a library of profiles can be used diagnostically to screen subjects by comparing the subject's profile with a profile representative of a comparable healthy or normal sample.

The following Example is meant to illustrate and not to limit the invention.

EXAMPLE

Identification of DNA by Raman Spectroscopy

Figure 5:
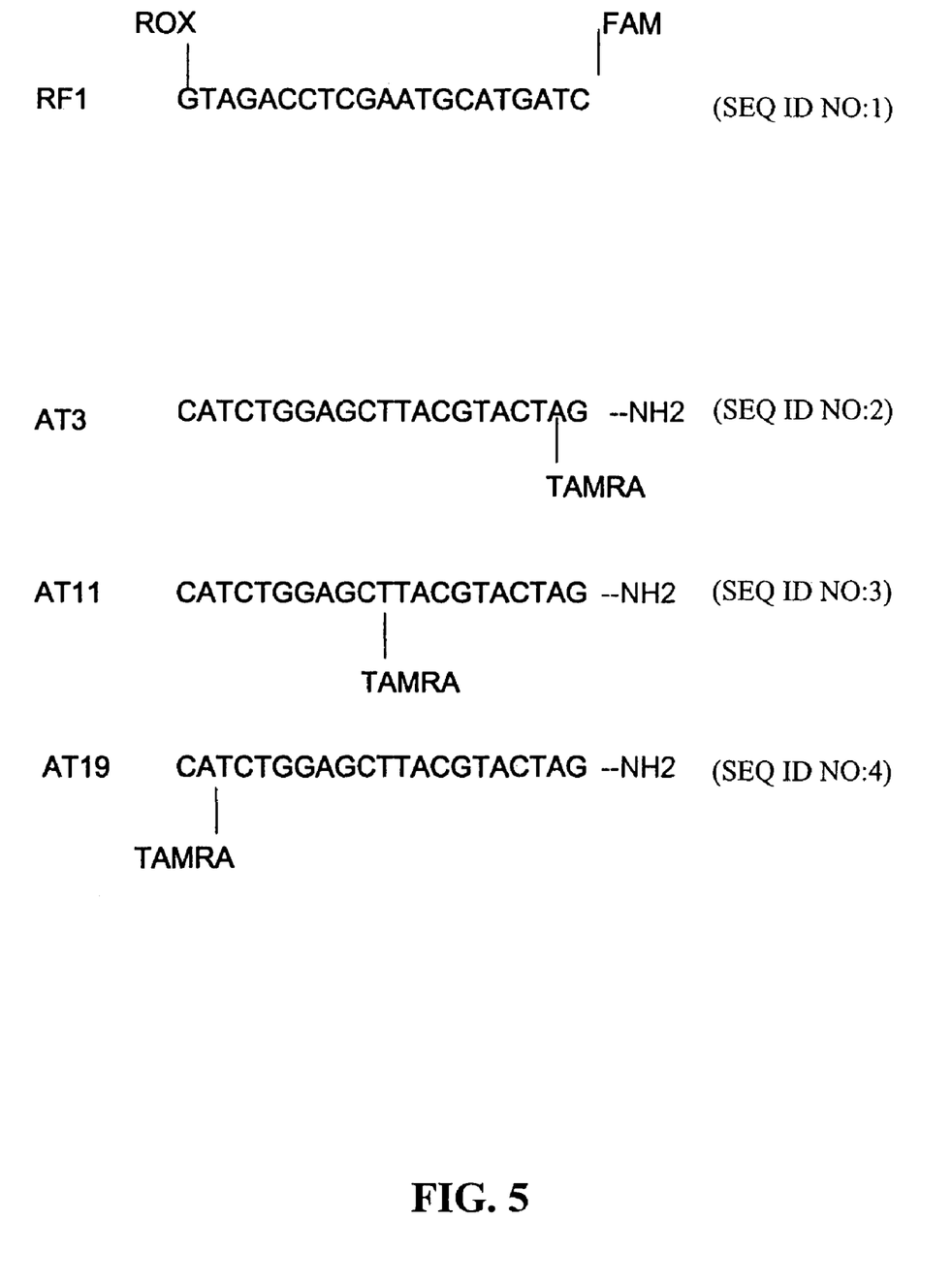
FIG. 5 shows one polynucleotide having fluorescence molecules ROX and FAM at opposite ends of the molecule and three single stranded DNA of identical sequence labeled with a fluorescence molecule, TAMRA, at different locations on the DNA. Depending upon the location of the label, the labeled DNA molecules generate unique Raman signals.
Figure 6:
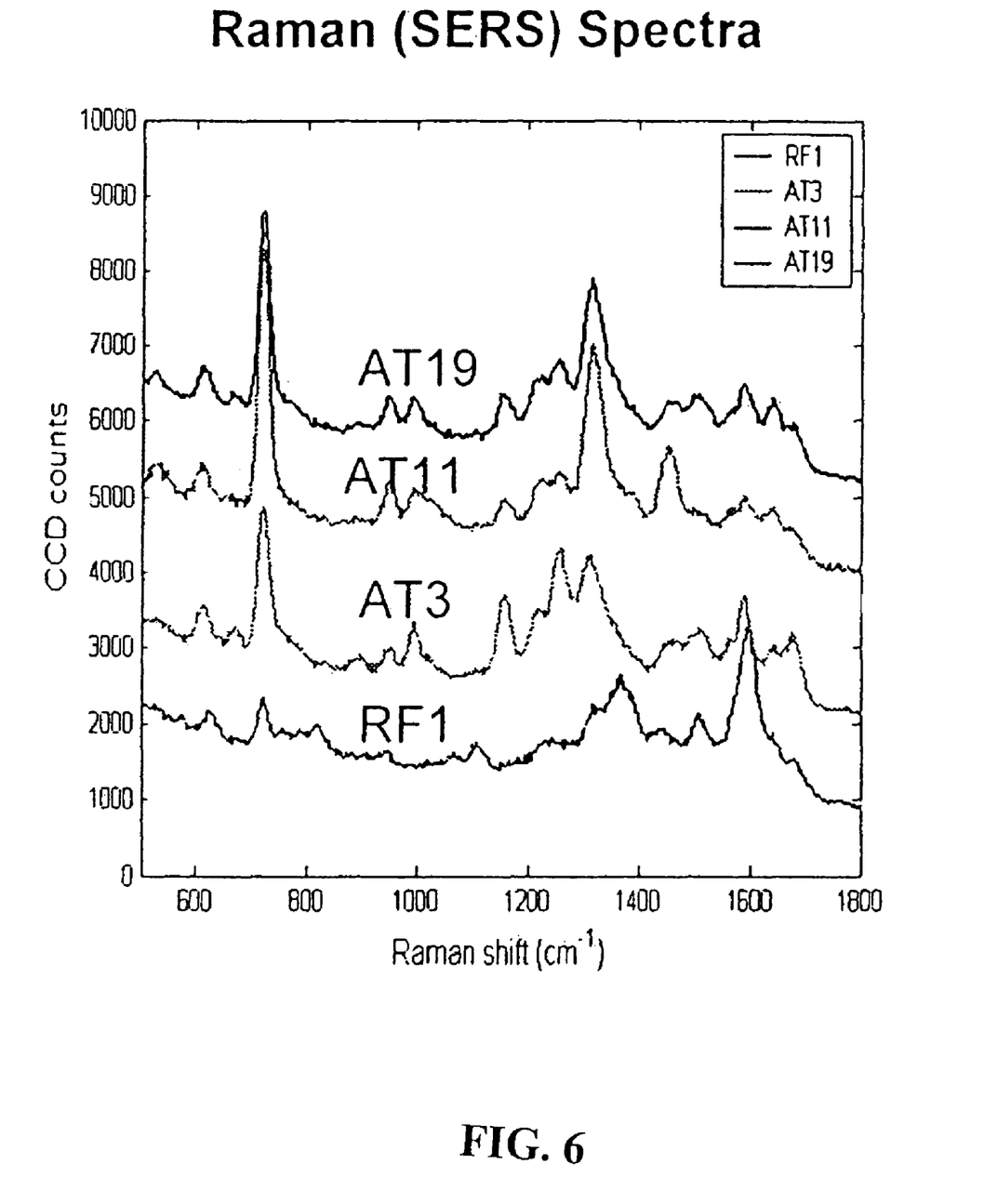
FIG. 6 is a graph showing Raman spectra produced by the four Raman-labeled single stranded DNA molecules of FIG. 5.

Single stranded DNA of identical sequence was labeled with a fluorescence molecule, TAMRA, at different locations (FIG. 4). Depending on the location of labeling, the labeled DNA molecules generated unique Raman signal, as shown in FIG. 5.

Although preferred embodiments have been depicted and described in detail herein, it will be apparent to those skilled in the relevant art that various modifications, additions, substitutions, and the like, can be made without departing from the spirit of the invention and these are therefore considered to be within the scope of the invention as defined in the claims which follow.

What is claimed is:

1. A detection system comprising:
    a nanoporous biological sensor comprising:
        a porous semiconductor structure comprising a central layer interposed between upper and lower layers, each of the upper and lower layers including strata of alternating porosity, wherein said porous semiconductor structure produces fluorescence upon illumination;
        at least one first probe bound to said semiconductor structure, wherein said first probe is disposed to bind an analyte molecule;
    an illumination source positioned to illuminate the biological sensor and cause the biological sensor to produce fluorescence;
    at least one Raman-active, second probe, wherein said second probe is disposed to bind said analyte molecule, and wherein said Raman-active, second probe is disposed to be indirectly irradiated by the fluorescence produced by said biological sensor; and
    a Raman detector positioned to capture Raman signals from complexes bound to the sensor.

2. The system of claim 1 further comprising another detector positioned to capture photoluminescent emissions from the biological sensor and to detect changes in photoluminescent emissions from the biological sensor upon binding of biological molecule to one or more pores in the structure.

3. The detection system of claim 1, wherein the source of illumination is a mercury or tungsten lamp.

4. The detection system of claim 1, wherein the porous semiconductor structure comprises p-doped silicon, n-doped silicon, intrinsic or undoped silicon, polysilicon, alloys thereof with germaniuin, mixtures thereof or semiconductor materials based on Group III element nitrides.

5. The detection system of claim 1, wherein the porous semiconductor structure comprises a surface area from about 90 $m^2/cm^3$ to about 783 $m^2/cm^3$.

6. The detection system of claim 1, wherein the porous semiconductor comprises pores having diameters that range from about 2 nm to about 2000 nm.

7. The detection system of claim 1, wherein the porosity of the central layer is about 50 to about 90 percent.

8. The detection system of claim 1, wherein the upper and lower layers individually contain strata of an alternating first and second porosity, wherein the first and second porosities are different.

9. The detection system of claim 8, wherein the strata comprise a plurality of first and second stratum, wherein each of plurality of first stratum have a different first porosity and each of the second stratum have a different second porosity.

10. The detection system of claim 1, further comprising probes bound to the porous semiconductor structure.

11. The detection system of claim 10, wherein the probes are throughout the central layer, upper layer, and lower layer of the porous semiconductor structure.

12. The detection system of claim 1, further comprising a coupling structure bound to the porous semiconductor structure.

13. The detection system of claim 1, wherein the system is configured to detect a change in refractive index.

14. The detection system of claim 1, wherein the system is configured to detect multiple layers of biomolecular interactions.

15. A detection system comprising:
    a nanoporous biological sensor comprising:
        a porous semiconductor structure comprising a central layer interposed between upper and lower layers, each of the upper and lower layers including strata of alternating porosity, wherein said porous semiconductor structure produces fluorescence upon illumination;
        at least one first probe bound to said semiconductor structure, wherein said first probe is disposed to bind an analyte molecule;

an illumination source positioned to illuminate the biological sensor and cause the biological sensor to produce fluorescence;

at least one Raman-active, second probe, wherein said second probe is disposed to bind said analyte molecule, and wherein said Raman-active, second probe is disposed to be indirectly irradiated by the fluorescence produced by said biological sensor; and a Raman detector positioned to capture Raman signals from complexes bound to the sensor;

wherein said upper layer further comprises a layer of a transparent metal.

16. The detection system of claim 15, wherein the transparent metal is roughened.

* * * * *

```
                        SEQUENCE LISTING

<160> NUMBER OF SEQ ID NOS: 2

<210> SEQ ID NO 1
<211> LENGTH: 21
<212> TYPE: DNA
<213> ORGANISM: Artificial
<220> FEATURE:
<223> OTHER INFORMATION: synthetic polynucleotide

<400> SEQUENCE: 1
gtagacctcg aatgcatgat c                                            21

<210> SEQ ID NO 2
<211> LENGTH: 21
<212> TYPE: DNA
<213> ORGANISM: Artificial
<220> FEATURE:
<223> OTHER INFORMATION: synthetic polynucleotide

<400> SEQUENCE: 2
catctggagc ttacgtacta g                                            21
```